United States Patent
Huang et al.

(10) Patent No.: US 6,391,645 B1
(45) Date of Patent: *May 21, 2002

(54) METHOD AND APPARATUS FOR CORRECTING AMBIENT TEMPERATURE EFFECT IN BIOSENSORS

(75) Inventors: Dijia Huang, Granger; Brenda L. Tudor; Kin-Fai Yip, both of Elkhart, all of IN (US)

(73) Assignee: Bayer Corporation, Elkhart, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 558 days.

(21) Appl. No.: 08/854,440

(22) Filed: May 12, 1997

(51) Int. Cl.[7] ............................................. G01N 27/12
(52) U.S. Cl. ........................ 436/95; 436/151; 422/82.02
(58) Field of Search .................. 422/82.02; 436/95, 436/151, 152; 435/14, 25, 287.1, 817; 205/777.5

(56) References Cited

U.S. PATENT DOCUMENTS

| | | | | |
|---|---|---|---|---|
| 4,431,004 A | * | 2/1984 | Bessman et al. ............. | 128/635 |
| 4,750,496 A | * | 6/1988 | Reinhart et al. ............. | 128/635 |
| 5,366,609 A | * | 11/1994 | White et al. ................. | 204/403 |
| 5,395,504 A | * | 3/1995 | Saurer et al. ............... | 204/403 |
| 5,508,171 A | * | 4/1996 | Walling et al. ........... | 205/777.5 |

* cited by examiner

Primary Examiner—Jeffrey Snay
(74) Attorney, Agent, or Firm—Jerome L. Jeffers

(57) ABSTRACT

A method and apparatus are provided for correcting ambient temperature effect in biosensors. An ambient temperature value is measured. A sample is applied to the biosensors, then a current generated in the test sample is measured. An observed analyte concentration value is calculated from the current through a standard response curve. The observed analyte concentration is then modified utilizing the measured ambient temperature value to thereby increase the accuracy of the analyte determination. The analyte concentration value can be calculated by solving the following equation:

$$G_2 = \frac{G_1 - (T_2^2 - 24^2)*I2 - (T_2 - 24)*I1}{(T_2^2 - 24^2)*S2 + (T_2 - 24)*S1 + 1}$$

where $G_1$ is said observed analyte concentration value, $T_2$ is said measured ambient temperature value and I1, I2, S1, and S2 are predetermined parameters.

12 Claims, 2 Drawing Sheets

METHOD AND APPARATUS FOR CORRECTING AMBIENT TEMPERATURE EFFECT IN BIOSENSORS

FIELD OF THE INVENTION

The present invention relates to a biosensor, and, more particularly, to a new and improved method and apparatus for correcting ambient temperature effect in biosensors.

DESCRIPTION OF THE PRIOR ART

The quantitative determination of analytes in body fluids is of great importance in the diagnoses and maintenance of certain physiological abnormalities. For example lactate, cholesterol and bilirubin should be monitored in certain individuals. In particular, the determination of glucose in body fluids is of great importance to diabetic individuals who must frequently check the level of glucose in their body fluids as a means of regulating the glucose intake in their diets. While the remainder of the disclosure herein will be directed towards the determination of glucose, it is to be understood that the procedure and apparatus of this invention can be used for the determination of other analytes upon selection of the appropriate enzyme. The ideal diagnostic device for the detection of glucose in fluids must be simple, so as not to require a high degree of technical skill on the part of the technician administering the test. In many cases, these tests are administered by the patient which lends further emphasis to the need for a test which is easy to carry out. Additionally, such a device should be based upon elements which are sufficiently stable to meet situations of prolonged storage.

Methods for determining analyte concentration in fluids can be based on the electrochemical reaction between an enzyme and the analyte specific to the enzyme and a mediator which maintains the enzyme in its initial oxidation state. Suitable redox enzymes include oxidases, dehydrogenases, catalase and peroxidase. For example, in the case where glucose is the analyte, the reaction with glucose oxidase and oxygen is represented by equation (A).

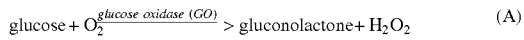
(A)

In a calorimetric assay, the released hydrogen peroxide, in the presence of a peroxidase, causes a color change in a redox indicator which color change is proportional to the level of glucose in the test fluid. While calorimetric tests can be made semi-quantitative by the use of color charts for comparison of the color change of the redox indicator with the color change obtained using test fluids of known glucose concentration, and can be rendered more highly quantitative by reading the result with a spectrophotometric instrument, the results are generally not as accurate nor are they obtained as quickly as those obtained using an electrochemical biosensor. As used herein, the term biosensor is intended to refer to an analytical device that responds selectively to analytes in an appropriate sample and converts their concentration into an electrical signal via a combination of a biological recognition signal and a physico-chemical transducer. Aside from its greater accuracy, a biosensor is an instrument which generates an electrical signal directly thereby facilitating a simplified design. Furthermore, a biosensor offers the advantage of low material cost since a thin layer of chemicals is deposited on the electrodes and little material is wasted.

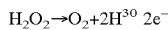
(B)

The electron flow is then converted to the electrical signal which directly correlates to the glucose concentration.

In the initial step of the reaction represented by equation (A), glucose present in the test sample converts the oxidized flavin adenine dinucleotide (FAD) center of the enzyme into its reduced form, ($FADH_2$).

Because these redox centers are essentially electrically insulated within the enzyme molecule, direct electron transfer to the surface of a conventional electrode does not occur to any measurable degree in the absence of an unacceptably high overvoltage. An improvement to this system involves the use of a nonphysiological redox coupling between the electrode and the enzyme to shuttle electrons between the ($FADH_2$) and the electrode. This is represented by the following scheme in which the redox coupler, typically referred to as a mediator, is represented by M:

$$Glucose+GO(FAD) \rightarrow gluconolactone+GO(FADH_2)$$

$$GO(FADH_2)+2M_{OX} \rightarrow GO(FAD)+2M_{red}+2H$$

$$2M_{red} \rightarrow 2M_{OX}+2e^- \text{(at the electrode)}$$

In this scheme, GO(FAD) represents the oxidized form of glucose oxidase and GO($FADH_2$) indicates its reduced form. The mediating species $M_{red}$ shuttles electrons from the reduced enzyme to the electrode thereby oxidizing the enzyme causing its regeneration in situ which, of course, is desirable for reasons of economy. The main purpose for using a mediator is to reduce the working potential of the sensor. An ideal mediator would be re-oxidized at the electrode at a low potential under which impurity in the chemical layer and interfering substances in the sample would not be oxidized thereby minimizing interference.

Many compounds are useful as mediators due to their ability to accept electrons from the reduced enzyme and transfer them to the electrode. Among the mediators known to be useful as electron transfer agents in analytical determinations are the substituted benzo and naphthoquinones disclosed in U.S. Pat. No. 4,746,607; the N-oxides, nitroso compounds, hydroxylamines and oxines specifically disclosed in EP 0 354 441; the flavins, phenazines, phenothiazines, indophenols, substituted 1,4-benzoquinones and indamins disclosed in EP 0 330 517 and the phenazinium/phenoxazinium salts described in U.S. Pat. No. 3,791,988. A comprehensive review of electrochemical mediators of biological redox systems can be found in *Analytica Clinica Acta.* 140 (1982), Pp 1–18.

Among the more venerable mediators is hexacyanoferrate, also known as ferricyanide, which is discussed by Schläpfer et al in *Clinica Chimica Acta.*, 57 (1974), Pp. 283–289. In U.S. Pat. No. 4,929,545 there is disclosed the use of a soluble ferricyanide compound in combination with a soluble ferric compound in a composition for enzymatically determining an analyte in sample. Substituting the iron salt of ferricyanide for oxygen in equation (A) provides:

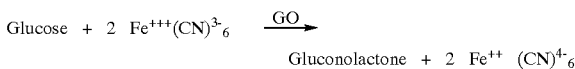

since the ferricyanide is reduced to ferrocyanide by its acceptance of electrons from the glucose oxidase enzyme.

Another way of expressing this reaction is by use of the following equation (C):

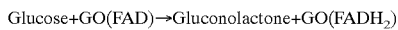

$$GO(FADH_2) + 2FE(CN_3)^{3-}{}_6 \rightarrow GO(FAD) + 2FE(CN)_6{}^{4-} + 2H^+$$

$$2FE(CN)_6{}^{4-} \rightarrow 2FE(CN)_6{}^{3-} + 2e^- \text{(at the electrode)} \qquad (C)$$

The electrons released are directly proportional to the amount of glucose in the test fluid and can be related thereto by measurement of the current which is produced upon the application of a potential thereto. Oxidation of the ferrocyanide at the anode renews the cycle.

SUMMARY OF THE INVENTION

Important objects of the present invention are to provide a new and improved method and apparatus for correcting ambient temperature effect in biosensors; to provide such method and apparatus that eliminates or minimizes the ambient temperature effect in analyte concentration value identified by a biosensor; and to provide such method and apparatus that overcome many of the disadvantages of prior art arrangements.

In brief, a method and apparatus are provided for correcting ambient temperature effect in biosensors. An ambient temperature value is measured. A sample is applied to the biosensors, then a current generated in the test sample is measured. An observed analyte concentration value is calculated from the current through a standard response curve. The observed analyte concentration is then modified utilizing the measured ambient temperature value to thereby increase the accuracy of the analyte determination.

In accordance with a feature of the invention, the analyte concentration value is calculated by solving the following equation:

$$G_2 = \frac{G_1 - (T_2^2 - 24^2)*I2 - (T_2 - 24)*I1}{(T_2^2 - 24^2)*S2 + (T_2 - 24)*S1 + 1}$$

where $G_1$ is said observed analyte concentration value, $T_2$ is said measured ambient temperature value and I1, I2, S1, and S2 are predetermined parameters.

Brief Description of the Drawing

The present invention together with the above and other objects and advantages may best be understood from the following detailed description of the preferred embodiments of the invention illustrated in the drawings, wherein.

DETAILED DESCRIPTION OF THE PREFERRED EMBODIMENTS

Figure 1:
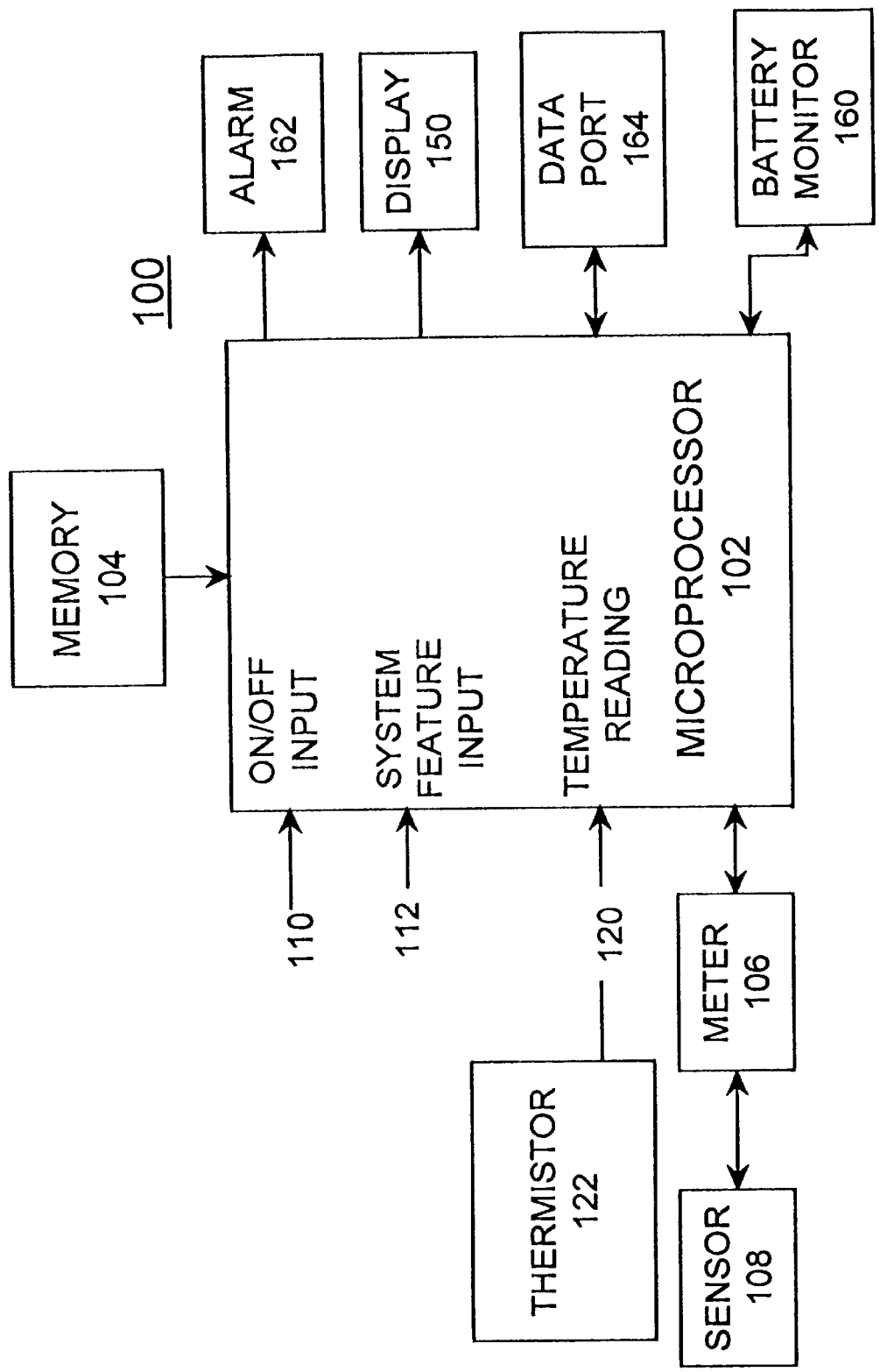
FIG. 1 is a block diagram representation of biosensor in accordance with the present invention.

Having reference now to the drawings, in FIG. 1 there is shown a block diagram representation of biosensor system designated as a whole by the reference character 100 and arranged in accordance with principles of the present invention. Biosensor system 100 includes a microprocessor 102 together with an associated memory 104 for storing program and user data. A meter function 106 coupled to biosensor 108 is operatively controlled by the microprocessor 102 for recording test values, such as blood glucose test values. An ON/OFF input at a line 110 responsive to the user ON/OFF input operation is coupled to the microprocessor 102 for performing the blood test sequence mode of biosensor system 100. A system features input at a line 112 responsive to a user input operation is coupled to the microprocessor 102 for selectively performing the system features mode of biosensor 100. A signal input indicated at a line 120 is coupled to the microprocessor 102 providing temperature information from a thermistor 122 in accordance with the invention. Microprocessor 102 contains suitable programming to perform the methods of the invention as illustrated in FIG. 2.

A display 150 is coupled to the microprocessor 102 for displaying information to the user including test results. A battery monitor function 160 is coupled to the microprocessor 102 for detecting a low or dead battery condition. An alarm function 162 is coupled to the microprocessor 102 for detecting predefined system conditions and for generating alarm indications for the user of biosensor system 100. A data port or communications interface 164 couples data to and from a connected computer (not shown).

In accordance with the invention, to reduce the temperature bias, biosensor system 100 performs a temperature correction method of the preferred embodiment.

Figure 2:
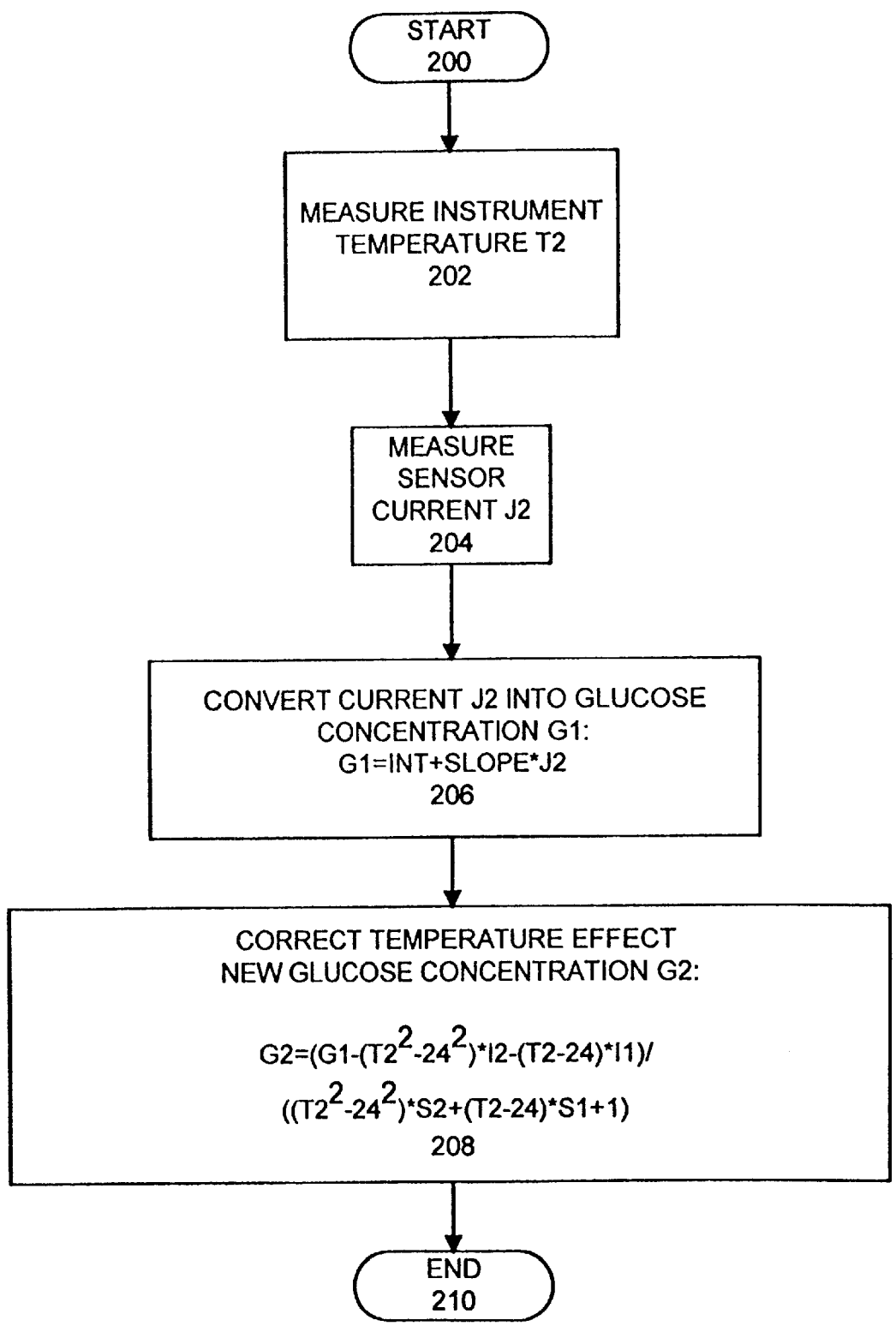
FIG. 2 is a flow chart illustrating logical steps performed in accordance with the present invention of the method correcting ambient temperature effect in biosensors by the biosensor of FIG. 1.

Referring to FIG. 2, logical steps performed in accordance with the method for correcting ambient temperature effect in biosensors 108 by the biosensor processor 102 begin at block 200. First ambient temperature is measured as indicated at a block 202 labeled MEASURE INSTRUMENT TEMPERATURE T2. Then sensor current is measured as indicated at a block 204. Next the measured current value is converted into an analyte concentration value, such as glucose concentration value (observed concentration), as indicated at a block 206. Then correction for temperature effect is performed in a final glucose concentration calculation as indicated at a block 208. The temperature corrected glucose concentration is calculated utilizing the following equation:

$$G_2 = \frac{G_1 - (T_2^2 - 24^2)*I2 - (T_2 - 24)*I1}{(T_2^2 - 24^2)*S2 + (T_2 - 24)*S1 + 1}$$

where $G_1$ is said observed analyte concentration value, $T_2$ is said measured ambient temperature value and I1, I2, S1, and S2 are predetermined parameters. This completes the sequence as indicated at a block 210.

Amperometric biosensors 108 are known to be sensitive to temperature. This temperature effect occurs because diffusion of the mediator to the working electrode is temperature dependent. Diffusion typically induces a temperature effect of 1–2% bias per degree centigrade. Therefore temperatures as low as 10° C. would produce results with a bias of about −25% and temperatures as high as 40° C. would produce results with a bias about +25%. The system 100 instrument provides results between 0 to 50° C. The only available temperature measurement comes from a thermistor inside the instrument. In order to reduce the temperature bias it was necessary to develop a temperature correction algorithm.

The temperature effect was determined experimentally by biosensor system 100 whole blood glucose assay over the entire glucose (50 to 600 mg/dL) and temperature range (10 to 40° C.) expected to be A encountered. Actual blood glucose readings and sample temperatures were measured. This was done for six different sensor 108 lots. When the "compound interest" temperature correction method was used, several lots had percent biases of −10% to −13% at the extreme temperatures. The formula for the "compound interest" correction method is:

$$G_2 = G_1 * (1+tc/100)^{25-T} \quad \text{Equation 1}$$

where $G_1$ is the observed glucose concentration, tc is the temperature coefficient determined experimentally and T is the sample temperature.

The "compound interest" algorithm did not work well because the temperature coefficient, tc, changed with glucose concentration. A "polynomial" correction algorithm was invented to handle the varying temperature coefficient problem. By using a polynomial correction algorithm, the percent bias was limited to within +/-10%. The equation for the polynomial correction method is described in Equation #2. The grand sum of the absolute bias for both methods indicated that the polynomial correction method had less overall bias. Also, at the very extreme temperatures of 2 and 49° C., the polynomial correction method had lower bias (below 13.5%) where as the compound interest method was as high as -25%.

Therefore, the polynomial correction method provided an improvement over the "compound interest" correction method.

After running the glucose assay at different temperatures the current response at each temperature was calculated through the 24° C. (sample temperature) standard response curve to obtain the observed glucose concentration.

The observed glucose concentration and the sample temperature were then used to calculate the corrected glucose concentration using the following equation:

$$G_2 = \frac{G_1 - (T_2^2 - 24^2)*I2 - (T_2 - 24)*I1}{(T_2^2 - 24^2)*S2 + (T_2 - 24)*S1 + 1} \quad \text{Equation 2}$$

where $G_1$ is the observed glucose concentration, $T_2$ is the sample temperature and I1, I2, S1, and S2 are the predetermined coefficients. These coefficients were determined experimentally. See the following exemplary procedure for details.

Table 1 shows an example of the temperature correction results. $T_2$ is the sample temperature. $G_R$ is the reference glucose valve. I is the measured current. $G_1$ is the observed glucose concentration (without temperature correction). % B is the percent bias without temperature correction. $G_2$ is the temperature corrected glucose concentration. % $B_C$ is the percent bias after temperature correction.

The data shows the percent bias before and after the correction algorithm was applied. The algorithm and coefficients were able to reduce the percent bias at the extreme temperatures of 10 to 40° C. to within +/-7%.

EXAMPLE

TABLE 1

Temperature Correction for Lot C
I1  0.17706
I2  -0.0086
S1  0.01529
S2  0.00004

Lot C

| $T_2$ | $G_R$ | I | $G_1$ | % B | $G_2$ | % $B_C$ |
|---|---|---|---|---|---|---|
| 8.7 | 50 | 1024 | 38.3 | -23.4% | 49.1 | -1.8% |
| 8.7 | 100 | 1484 | 78.6 | -21.4% | 102.9 | 2.9% |
| 8.7 | 200 | 2404 | 159.1 | -20.5% | 210.6 | 5.3% |
| 8.7 | 400 | 4243 | 320.1 | -20.0% | 426.0 | 6.5% |
| 8.7 | 600 | 6082 | 481.2 | -19.8% | 641.4 | 6.9% |
| 16.7 | 50 | 1109 | 45.7 | -8.6% | 50.6 | 1.3% |

TABLE 1-continued

Temperature Correction for Lot C
I1  0.17706
I2  -0.0086
S1  0.01529
S2  0.00004

Lot C

| $T_2$ | $G_R$ | I | $G_1$ | % B | $G_2$ | % $B_C$ |
|---|---|---|---|---|---|---|
| 16.7 | 100 | 1608 | 89.4 | -10.6% | 100.4 | 0.4% |
| 16.7 | 200 | 2606 | 176.8 | -11.6% | 199.9 | 0.0% |
| 16.7 | 400 | 4602 | 351.6 | -12.1% | 398.3 | -0.3% |
| 16.7 | 600 | 6598 | 526.4 | -12.3% | 597.9 | -0.3% |
| 23.9 | 50 | 1158 | 50.0 | 0.0% | 50.0 | 0.0% |
| 23.9 | 100 | 1729 | 100.0 | 0.0% | 100.0 | 0.0% |
| 23.9 | 200 | 2871 | 200.0 | 0.0% | 200.0 | 0.0% |
| 23.9 | 400 | 5155 | 400.0 | 0.0% | 400.0 | 0.0% |
| 23.9 | 600 | 7439 | 600.0 | 0.0% | 600.0 | 0.0% |
| 30.6 | 50 | 1212 | 54.7 | 9.5% | 50.8 | 1.5% |
| 30.6 | 100 | 1851 | 110.6 | 10.6% | 100.8 | 0.8% |
| 30.6 | 200 | 3128 | 222.5 | 11.2% | 200.9 | 0.5% |
| 30.6 | 400 | 5682 | 446.1 | 11.5% | 401.1 | 0.3% |
| 30.6 | 600 | 8236 | 669.8 | 11.6% | 601.3 | 0.2% |
| 38.2 | 50 | 1251 | 58.1 | 16.2% | 50.4 | 0.8% |
| 38.2 | 100 | 2008 | 124.4 | 24.4% | 103.3 | 3.3% |
| 38.2 | 200 | 3522 | 257.0 | 28.5% | 209.0 | 4.5% |
| 38.2 | 400 | 6550 | 522.1 | 30.5% | 420.4 | 5.1% |
| 38.2 | 600 | 9578 | 787.3 | 31.2% | 631.8 | 5.3% |

The following describes an exemplary procedure used for determining the temperature correction coefficients ($I_1$, $I_2$, $S_1$, $S_2$ in Equation 2). First venous heparinized whole blood (~45% hematocrit) from a single donor was spiked close to different glucose concentrations (values determined by the Yellow Springs Instrument, YSI, reference method and corrected for any known sample interferences) and tested in system 100 instruments at different environmental chamber temperatures (Table 1, e.g. samples of 50 and 400 mg/dL glucose at 8.7, 16.7, 23.9, 30.6 and 38.2° $C_x$.) The Yellow Springs Instrument and method are described by Conrad et al., in the February 1989 "Journal of Pediatrics" Pages 281–287 and by Burmeister et al., in "Analytical Letters", 28(4), 581–592 (1995). High relative humidity (65 to 85%) was maintained in the chamber in order to prevent evaporative cooling, and the sample was equilibrated to the chamber temperature; this way the temperature effect would result only from the chemistry. The actual sample temperature was measured for each glucose spike. To determine the sample temperature, a 0.0005" thermocouple was inserted into a sensor without chemistry, and temperature data was collected every second after the blood was added to the sensor.

TABLE 2

Lot C Actual YSI Glucose and Current Response

| Sample Temp. | YSI | Current | Slope | Intercept |
|---|---|---|---|---|
| 8.7° C. | 54.2 | 1063 | | |
| 8.7° C. | 412.5 | 4358 | 9.20 | 564.6 |
| 16.7° C. | 54.9 | 1148 | | |
| 16.7° C. | 414.9 | 4750 | 9.98 | 610.2 |
| 23.9° C. | 55.7 | 1223 | | |
| 23.9° C. | 418 | 5359 | 11.42 | 587.1 |
| 30.6° C. | 49.3 | 1203 | | |
| 30.6° C. | 408.4 | 5787 | 12.77 | 573.7 |
| 38.2° C. | 51.6 | 1275 | | |
| 38.2° C. | 418.7 | 6833 | 15.14 | 493.8 |

Next, the current response at exactly 50, 100, 200, 400, and 600 mg/dL glucose for each temperature was determined through the curves using the slope and intercepts determined in Table 2. Using these calculated current values the observed glucose concentration was determined through the 24° C. curve as provided in Table 3.

TABLE 3

Lot C - Current Through the YSI 50 and 400 mg/dL Curves and the Observed Glucose mg/dL Through the 24° C. Curve

| Sample Temperature ° C. | YSI Reference Glucose mg/dL | Current | 23.9° C. Curve Observed Glucose mg/dL |
|---|---|---|---|
| 8.7 | 50 | 1024 | 38.3 |
| 8.7 | 100 | 1484 | 78.6 |
| 8.7 | 200 | 2404 | 159.1 |
| 8.7 | 400 | 4243 | 320.1 |
| 8.7 | 600 | 6082 | 481.2 |
| 16.7 | 50 | 1109 | 45.7 |
| 16.7 | 100 | 1608 | 89.4 |
| 16.7 | 200 | 2606 | 176.8 |
| 16.7 | 400 | 4602 | 351.6 |
| 16.7 | 600 | 6598 | 526.4 |
| 23.9 | 50 | 1158 | 50.0 |
| 23.9 | 100 | 1729 | 100.0 |
| 23.9 | 200 | 2871 | 200.0 |
| 23.9 | 400 | 5155 | 400.0 |
| 23.9 | 600 | 7439 | 600.0 |
| 30.6 | 50 | 1212 | 57.7 |
| 30.6 | 100 | 1851 | 110.6 |
| 30.6 | 200 | 3128 | 222.5 |
| 30.6 | 400 | 5682 | 446.1 |
| 30.6 | 600 | 8236 | 669.8 |
| 38.2 | 50 | 1251 | 58.1 |
| 38.2 | 100 | 2008 | 124.4 |
| 38.2 | 200 | 3522 | 257.0 |
| 38.2 | 400 | 6550 | 522.1 |
| 38.2 | 600 | 9578 | 787.3 |

Next for each spike of blood, the observed glucose concentration ($G_1$) was plotted against the sample temperature ($T_2$). The 2nd order polynomial curve was used to fit the plot and the a1 and a2 constants for that level of glucose were obtained as provided in Table 4. For example, a computer program such as Slidewrite by Advanced Graphics Software Inc., or any other equivalent curve fitting program can be used.

TABLE 4

Lot C - 2nd Order Polynomial Coefficients

| Coefficient | 50 mg/dL | 100 mg/dL | 200 mg/dL | 400 mg/dL | 600 mg/dL |
|---|---|---|---|---|---|
| a0 | 29.689 | 68.654 | 146.318 | 301.709 | 457.305 |
| a1 | 1.08071 | 1.06138 | 1.04494 | 1.00696 | 0.95187 |
| a2 | −0.00881 | 0.01035 | 0.04829 | 0.12417 | 0.20045 |
| Corr.Coef.R | 0.9990 | 1.000 | 0.9998 | 0.9996 | 0.9995 |

The a1 values obtained for the different levels of glucose mere plotted against the glucose concentration. The data was plotted using a linear fit, and the coefficients S1 (slope of the linear fit) and I1 (intercept of the linear fit) were generated. The Slidewrite program on a PC by Advanced Graphics Software Inc., or any other equivalent curve fitting program can be used.

The a2 values obtained for the different levels of glucose were also plotted against the glucose concentration. The data was plotted using a linear fit, and the coefficients S2 (slope of the linear fit) and I2 (intercept of the linear fit) were generated.

To derive the algorithm: at each level of glucose, the observed glucose concentration ($G_1$) is related to the sample temperature ($T_2$) in a 2nd order polynomial relationship.

$$G_1=(T_2^2)*a2+T_2*a1+a0 \quad \text{Or Equation 3}$$

And at a sample temperature of 24° C., $G_2$ (Corrected)=$G_1$ (Observed)

$$G_2=(24^2)*a2+24*a1+a0 \quad \text{Or Equation 4}$$

Subtracting equation (3) from equation (2) gives:

$$G_2-G_1=(T_2^2-24^2)*a2+(T_2-24)*a1 \quad \text{Equation 5}$$

From the linear plots generated at steps 4 and 5:

$$a1=S1*G_2+I1 \quad \text{Equation 6}$$

and $$a2=S2*G_2+I2 \quad \text{Equation 7}$$

Combining equation (5), (6), and (7) gives equation (2).

While the present invention has been described with reference to the details of the embodiments of the invention shown in the drawing, these details are not intended to limit the scope of the invention as claimed in the appended claims.

What is claimed is:

1. A method for correcting ambient temperature effect in biosensors comprising the steps of:

measuring an ambient temperature value;

applying a sample to the biosensors and measuring a current generated in the test sample;

calculating an analyte concentration value utilizing said measured ambient temperature value to thereby increase the accuracy of the analyte determination; and said step of calculating said analyte concentration value includes the step of converting said measured current to an observed analyte concentration value and calculating a corrected analyte concentration value utilizing the equation:

$$G_2 = \frac{G_1 - (T_2^2 - 24^2)*I2 - (T_2 - 24)*I1}{(T_2^2 - 24^2)*S2 + (T_2 - 24)*S1 + 1}$$

where $G_1$ is said observed analyte concentration value, $T_2$ is said measured ambient temperature value and I1, I2, S1, and S2 are set values and are experimentally determined coefficients.

2. A method for correcting ambient temperature effect in biosensors as recited in claim 1 wherein I1, I2, S1, and S2 are experimentally determined coefficients by sequentially providing a sample to a plurality of concentration values and measuring a resulting current response for each of the plurality of concentration values for each of a plurality of temperature values; generating plots of said observed analyte concentration values and using the following equations:

$$G_2-G_1=(T_2^2-24^2)*a2=(T_2+24)*a1$$

$$a1=S1*G_2+I_1$$

$$a2=S2*G_2+I_2$$

and the generated plots to determine I1, I2, S1, and S2.

3. A method for correcting ambient temperature effect in biosensors as recited in claim 1 wherein the analyte is glucose.

4. Apparatus for correcting ambient temperature effect in biosensors comprising:

means for measuring an ambient temperature value;

means responsive to an applied sample to the biosensors, for measuring a current generated in the test sample;

means for calculating an analyte concentration value utilizing said measured ambient temperature value to thereby increase the accuracy of the analyte determination; and wherein said means for calculating said analyte concentration value includes means for converting said measured current to an observed analyte concentration value and for calculating a corrected analyte concentration value utilizing the equation:

$$G_2 = \frac{G_1 - (T_2^2 - 24^2)*I2 - (T_2 - 24)*I1}{(T_2^2 - 24^2)*S2 + (T_2 - 24)*S1 + 1}$$

where $G_1$ is said observed analyte concentration value, $T_2$ is said measured ambient temperature value and I1, I2, S1, and S2 are set values and are experimentally determined coefficients.

5. Apparatus for correcting ambient temperature effect in biosensors as recited in claim 4 includes processor means for performing a predefined test sequence; and, wherein said means for measuring said ambient temperature value includes a thermistor coupled to said processor means.

6. Apparatus for correcting ambient temperature effect in biosensors as recited in claim 4 wherein I1, I2, S1, and S2 are experimentally determined coefficients by sequentially providing a sample to a plurality of concentration values and measuring a resulting current response for each of the plurality of concentration values for each of a plurality of temperature values; generating plots of said observed analyte concentration values and using the following equations:

$G_{2-G1}=(T_2^2-24^2)*a2+(T_2-24)*a1$ $a1=S1*G_2+I1$ $a2=S2*G_2+I2$ and the generated plots to determine I1, I2, S1, and S2.

7. Apparatus for correcting ambient temperature effect in biosensors as recited in claim 4 wherein the analyte is glucose.

8. Apparatus for correcting ambient temperature effect in biosensors as recited in claim 4 wherein said means responsive to said applied sample to the biosensors, for measuring said current generated in the test sample includes processor means coupled to the biosensors for receiving a signal representing said current generated in the test sample.

9. Apparatus for correcting ambient temperature effect in biosensors as recited in claim 4 wherein said means for calculating said analyte concentration value includes processor means coupled to said ambient temperature measuring means and said current measuring means and including means for solving said equation utilizing said measured values and predetermined coefficient values.

10. A biosensor comprising:

biosensors means for receiving a user sample;

processor means responsive to said user sample receiving means, for measuring a current generated in the test sample;

means for measuring an ambient temperature value; and means for calculating an analyte concentration value utilizing said measured ambient temperature value to thereby increase the accuracy of the analyte determination; and wherein said processor means includes means for converting said measured current to an observed analyte concentration value and for calculating a corrected analyte concentration value utilizing the equation:

$$G_2 = \frac{G_1 - (T_2^2 - 24^2)*I2 - (T_2 - 24)*I1}{(T_2^2 - 24^2)*S2 + (T_2 - 24)*S1 + 1}$$

where $G_1$ is said observed analyte concentration value, $T_2$ is said measured ambient temperature value and I1, I2, S1, and S2 are set values and are experimentally determined coefficients.

11. A biosensor as recited in claim 10 wherein I1, I2, S1, and S2 are experimentally determined coefficients by sequentially providing a sample to a plurality of concentration values and measuring a resulting current response for each of the plurality of concentration values for each of a plurality of temperature values, generating plots of said observed analyte concentration values and using the following equations:

$G_{2-G1}=(T_2^2-24^2)*a2+(T_2-24)*a1$ $a1=S1*G_2+I_1$ $a2=S2*G_2+I2$ and the generated plots to determine I1, I2, S1, and S2.

12. A biosensor as recited in claim 10 wherein said means for measuring said ambient temperature value include a thermistor coupled to said processor means.

* * * * *